(12) United States Patent
Montgomery et al.

(10) Patent No.: US 12,023,244 B2
(45) Date of Patent: Jul. 2, 2024

(54) DELIVERY DEVICE HAVING GUIDE WIRE CONTROL

(71) Applicant: Medtronic, Inc., Minneapolis, MN (US)

(72) Inventors: Stephen A. Montgomery, Athenry (IE); Ciaran McGuinness, Castlerea (IE)

(73) Assignee: MEDTRONIC, INC., Minneapolis, MN (US)

( * ) Notice: Subject to any disclaimer, the term of this patent is extended or adjusted under 35 U.S.C. 154(b) by 485 days.

(21) Appl. No.: 17/179,613

(22) Filed: Feb. 19, 2021

(65) Prior Publication Data

US 2021/0322165 A1    Oct. 21, 2021

Related U.S. Application Data

(60) Provisional application No. 63/010,325, filed on Apr. 15, 2020.

(51) Int. Cl.
*A61F 2/24* (2006.01)
*A61M 25/09* (2006.01)

(52) U.S. Cl.
CPC .. *A61F 2/2427* (2013.01); *A61M 2025/09116* (2013.01); *A61M 2025/09125* (2013.01)

(58) Field of Classification Search
None
See application file for complete search history.

(56) References Cited

U.S. PATENT DOCUMENTS

| | | |
|---|---|---|
| 5,201,757 A | 4/1993 | Heyn et al. |
| 6,533,772 B1 | 3/2003 | Sherts et al. |
| 6,752,800 B1 | 6/2004 | Winston et al. |
| 9,919,130 B2 | 3/2018 | Ring |
| 2013/0211508 A1* | 8/2013 | Lane .................. A61F 2/2427 623/2.11 |
| 2014/0094774 A1 | 4/2014 | Blanchard |
| 2014/0100552 A1 | 4/2014 | Gallacher et al. |

(Continued)

OTHER PUBLICATIONS

The International Search Report and Written Opinion for International Application No. PCT/US2021/025720 mailed Aug. 4, 2021 (10 pages).

(Continued)

*Primary Examiner* — Shaun L David
(74) *Attorney, Agent, or Firm* — Wentsler LLC

(57) ABSTRACT

The disclosure generally relates to delivery devices for transcatheter delivery of a prosthesis. The delivery device includes a hollow shaft on which the prosthesis is supported. A handle assembly maintains the shaft. The delivery device further includes a guide wire that is selectively directed through the handle assembly and shaft. The guide wire directs the shaft to a target site at which the prosthesis is to be deployed. In practice, an operator managing the inner catheter controls the prosthesis positioning. The delivery devices disclosed herein are configured to ergonomically also allow the operator to control the position of the guide wire as the position of the guide wire influences the deployment position of the prosthesis. In this way, a second operator for positioning the guide wire can be omitted. Embodiments of the disclosure are believed to improve positioning predictability and ease of use.

20 Claims, 4 Drawing Sheets

(56) References Cited

U.S. PATENT DOCUMENTS

| | | | |
|---|---|---|---|
| 2014/0135909 A1* | 5/2014 | Carr | A61F 2/2436 |
| | | | 623/2.11 |
| 2015/0142048 A1 | 5/2015 | Coleman et al. | |
| 2015/0306358 A1 | 10/2015 | Duffy et al. | |
| 2017/0209671 A1* | 7/2017 | Ring | A61M 25/09041 |
| 2019/0201223 A1 | 7/2019 | Roeder et al. | |
| 2019/0365550 A1 | 12/2019 | Lei | |

OTHER PUBLICATIONS

International Preliminary Report on Patentability and Search Report in corresponding International Application No. PCT/US2021/025720.

* cited by examiner

DELIVERY DEVICE HAVING GUIDE WIRE CONTROL

CROSS-REFERENCE TO RELATED APPLICATIONS

This Non-Provisional Patent Applications claims the benefit of the filing date of U.S. Provisional Patent Application Ser. No. 63/010,325, filed Apr. 15, 2020, entitled "DELIVERY DEVICE HAVING GUIDE WIRE CONTROL," the entire teachings of which are incorporated herein by reference.

FIELD

The present technology is generally related to transcatheter prosthesis delivery devices and methods controlling a guide wire of the delivery device.

BACKGROUND

Diseased or otherwise deficient heart valves can be repaired or replaced with an implanted prosthetic heart valve. Conventionally, heart valve replacement surgery is an open-heart procedure conducted under general anesthesia, during which the heart is stopped and blood flow is controlled by a heart-lung bypass machine. Traditional open surgery inflicts significant patient trauma and discomfort, and exposes the patient to a number of potential risks, such as infection, stroke, renal failure, and adverse effects associated with the use of the heart-lung bypass machine, for example.

Due to the drawbacks of open-heart surgical procedures, there has been an increased interest in minimally invasive and percutaneous replacement of cardiac valves. With percutaneous transcatheter (or transluminal) techniques, a prosthetic heart valve is compacted for delivery in a catheter and then advanced, for example, through an opening in the femoral artery and through the descending aorta to the heart, where the prosthetic heart valve is then deployed in the annulus of the valve to be restored (e.g., the aortic valve annulus). Although transcatheter techniques have attained widespread acceptance with respect to the delivery of conventional stents to restore vessel patency, only mixed results have been realized with percutaneous delivery of the more complex prosthetic heart valve.

The present disclosure provides improvements relating to transcatheter delivery devices.

SUMMARY

The techniques of this disclosure generally relate to delivery devices for transcatheter delivery of a prosthesis. The delivery device includes a hollow shaft on which the prosthesis is supported. A handle assembly maintains the shaft. The delivery device further includes a guide wire that is selectively directed through the handle assembly and shaft. The guide wire directs the shaft to a target site at which the prosthesis is to be deployed. In practice, an operator managing the shaft or inner catheter controls the prosthesis positioning. The delivery devices disclosed herein are configured to ergonomically also allow the operator to control the position of the guide wire as the position of the guide wire influences the deployment position of the prosthesis. In this way, a second operator for positioning the guide wire can be omitted. Embodiments of the disclosure are believed to improve positioning predictability and ease of use.

In one aspect, the present disclosure provides a delivery device including a handle assembly having a distal end and a proximal end. The handle assembly further including a body defining a lumen that extends from the distal end to the proximal end. The delivery device further includes a hollow shaft extending from the distal end of the handle assembly and a guide wire extending through the lumen. The delivery device also includes a guide wire control having an actuator positioned at the distal end of the handle assembly and a lock positioned at the proximal end of the handle assembly. The actuator is interconnected to the lock with a connector positioned within the lumen. The guide wire control has an unlocked state, wherein movement of the actuator correspondingly slides to advance the guide wire. The guide wire control also has a locked state in which longitudinal movement of the guide wire with respect to the body is prevented.

In another aspect, the disclosure provides methods of controlling a guide wire. The method can include providing a delivery device having a handle assembly with a distal end and a proximal end. The handle assembly further including a body defining a lumen that extends from the distal end to the proximal end. The delivery device further includes a hollow shaft extending from the distal end of the handle assembly and a guide wire control. The guide wire control includes an actuator positioned at the distal end of the handle assembly and a lock positioned at the proximal end of the handle assembly. The actuator being interconnected to the lock with a connector positioned within the lumen. In this example, the guide wire control is provided in an unlocked state. The method further includes positioning a guide wire through the lumen and directing the guide wire through the lumen and into a vasculature of a patient proximate a target site by movement of the actuator. The method also includes transitioning the lock to the locked state.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Specific embodiments of the present disclosure are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician. Although the present disclosure has been described with reference to preferred embodiments, workers skilled in the art will recognize that changes can be made in form and detail without departing from the spirit and scope of the present disclosure.

Figure 1:
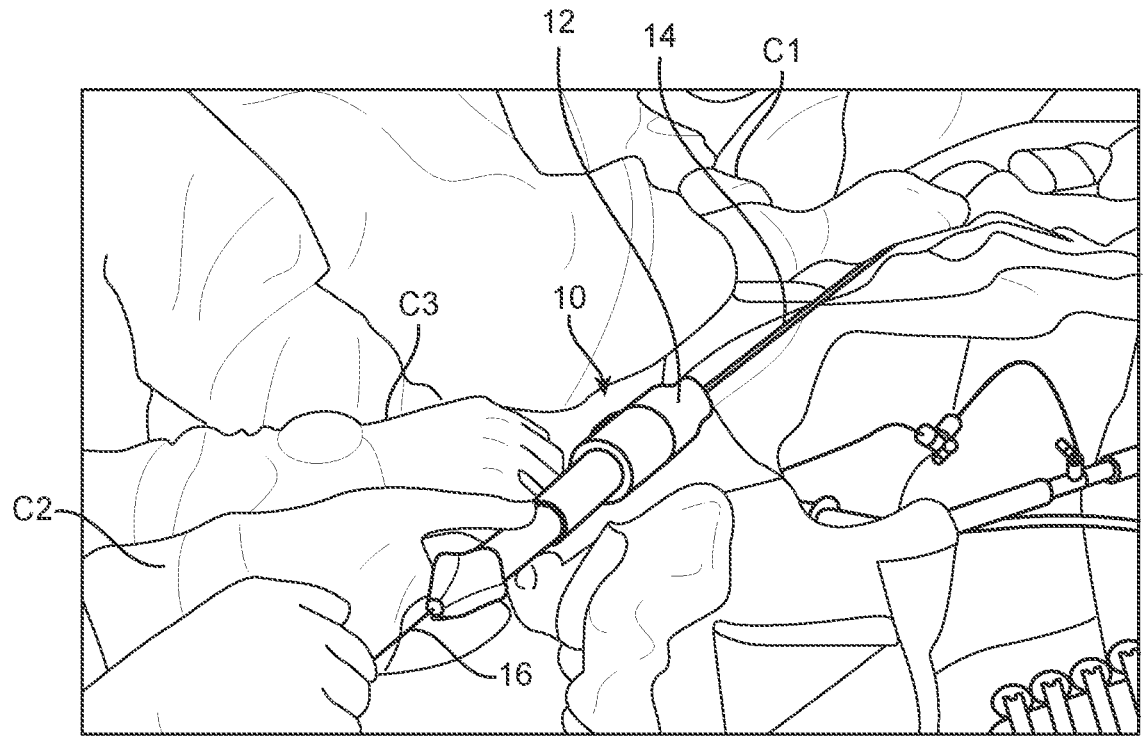
FIG. 1 illustrates three clinicians operating a delivery device.
Figure 2:
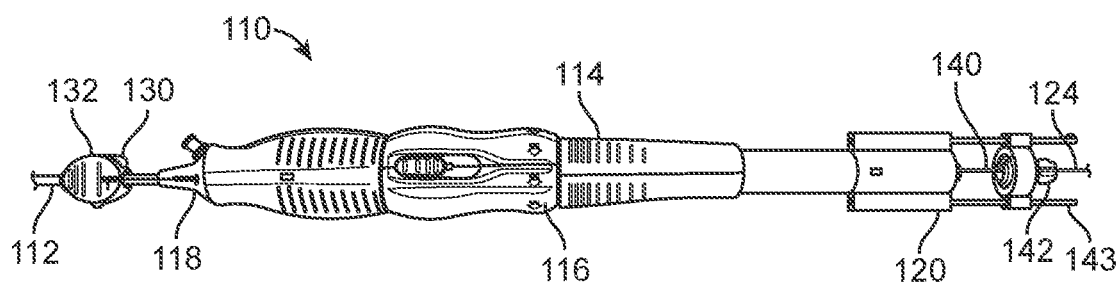
FIG. 2 is a partial, top view a delivery device of the disclosure having a guide wire control.
Figure 3:
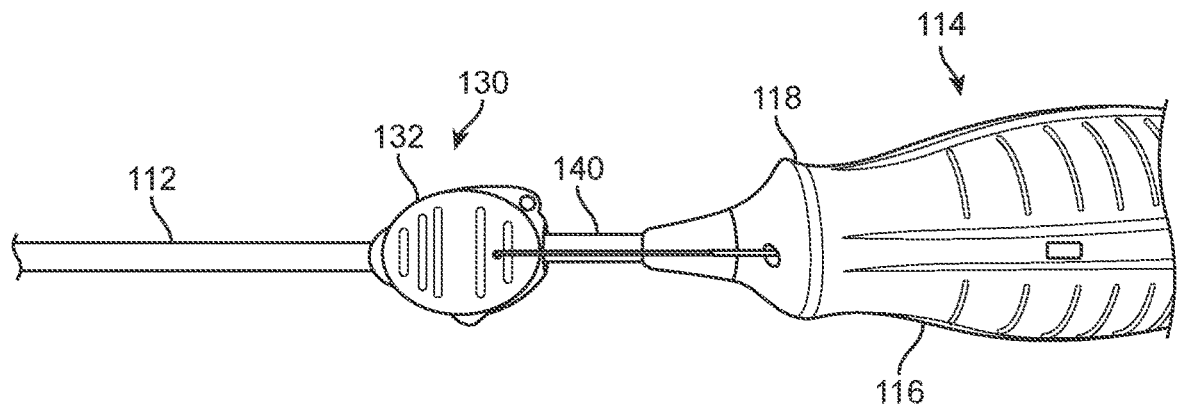
FIG. 3 is an enlarged top view of an actuator of the guide wire control of FIG. 2.
Figure 4:
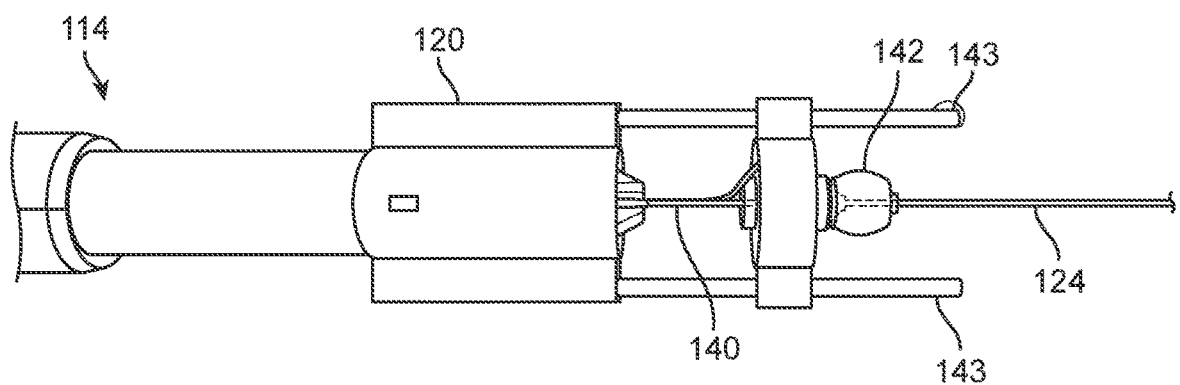
FIG. 4 is an enlarged top view of a lock of the guide wire control of FIG. 2.
Figure 5:
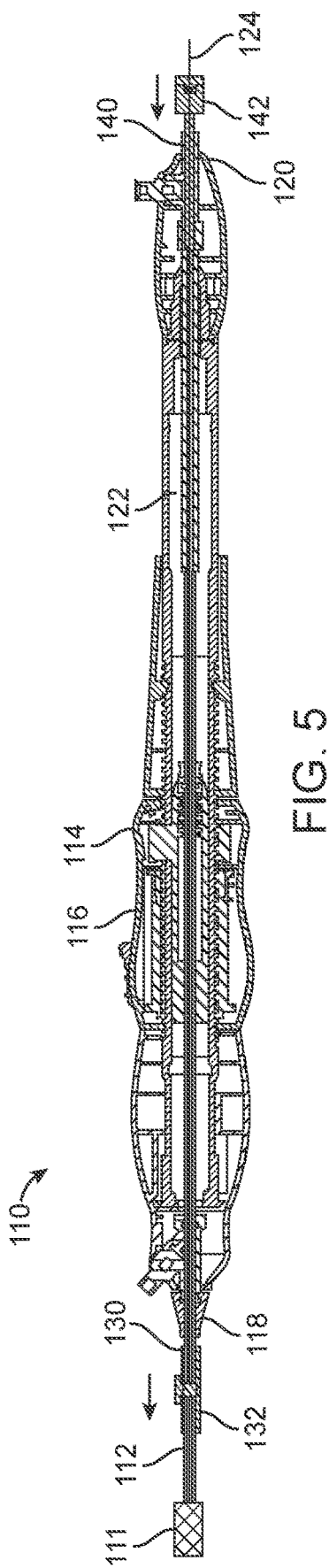
FIG. 5 is a cross-sectional view of the delivery device of FIG. 2.
Figure 6:
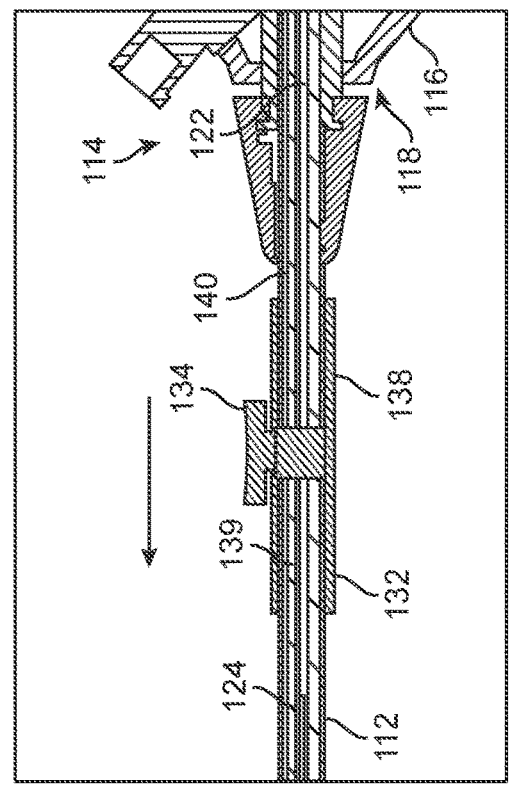
FIG. 6 is an enlarged, cross-sectional view of the actuator of FIGS. 2-3.
Figure 7:
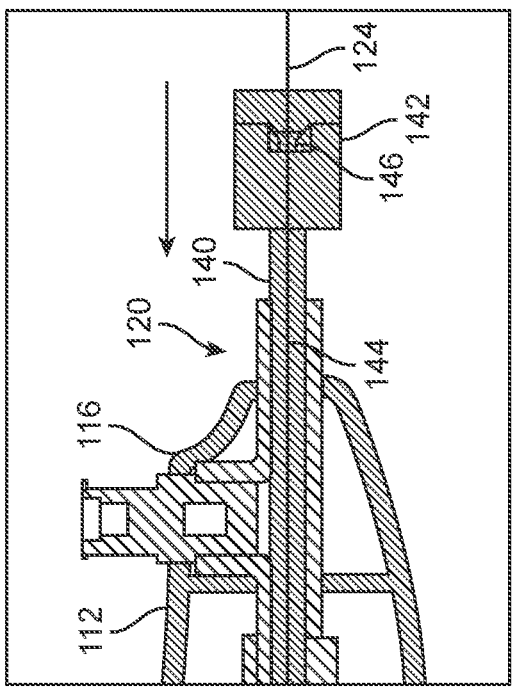
FIG. 7 is an enlarged, cross-sectional view of the lock of FIGS. 2 and 4.
Figure 8:
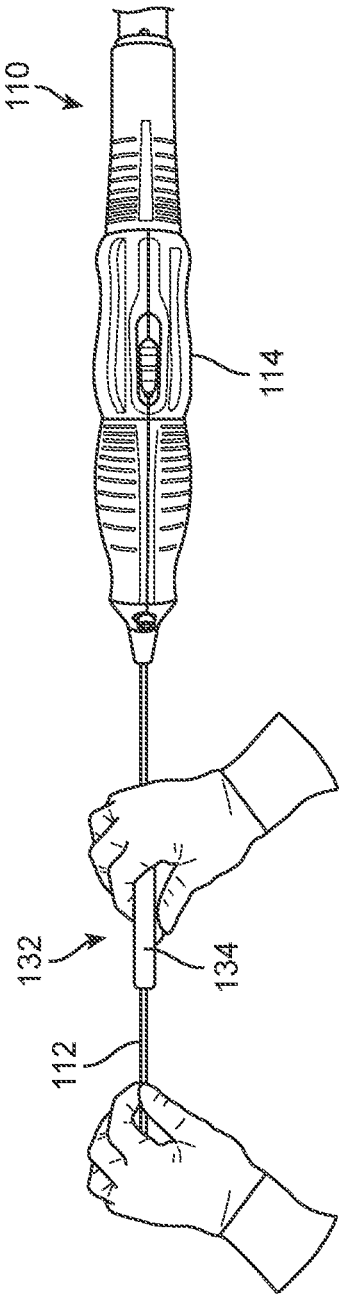
FIG. 8 illustrates optional hand placement for use of the actuator of the device of FIG. 2.

FIG. 1 illustrates two clinicians C1, C2 utilizing a delivery device 10 to deliver a prosthesis via a transcatehter procedure. The delivery device 10 can be of any known in the art that includes a handle assembly 12 connected to a hollow shaft 14 or the like on which the prosthesis (not visible) is supported. A guide wire 16 is provided and can be extended through the handle assembly 12 and shaft 14. In one example, the prosthesis is supported on the shaft 14 and an outer catheter (not shown) is provided to selectively sheathe the shaft 14 and prosthesis. The prosthesis could be one of a number of prosthesis such as a stent, prosthetic heart valve, for example. In such a procedure, the first clinician C1 manages and controls the shaft 14 and outer catheter management. For example, the first operator C1 controls a depth of the shaft (and optional outer catheter) during prosthesis deployment. A second operator C2 directs a guide wire 16 through a proximal end of a handle assembly 12 of the device to a distal end of the device 10, through the patient's vasculature to a target site. The second clinician C2 uses the guide wire for fine adjustment of the shaft/optional outer catheter and tension adjustment. It has been observed that with use of such delivery devices, the first operator C1 usually holds onto the shaft 14 or outer catheter with one hand and reaches with an underhanded grip to the guide wire 16. Then, the first operator C1 reaches over the second clinician C2 to move the guide wire 16, which is ergonomically awkward. Optionally, a third clinician C3 is provided to retract an outer catheter, if provided.

FIGS. 2-8 collectively illustrate a delivery device 110 for transcatheter delivery of a prosthesis 111. The delivery device 110 includes a hollow shaft 112 on which the prosthesis 111 is supported. It is noted that in FIG. 5 the shaft 112 is not shown to scale and shaft 112 is shown as foreshortened for ease of illustration. The shaft 112 may be significantly longer in practice. The delivery device 110 can further include an outer catheter (not shown) selectively sheathing the shaft 112 and prosthesis 111 during delivery. A handle assembly 114 maintains the shaft 112 and outer catheter. In some embodiments, the handle assembly 114 is configured to allow an operator to control movement of the outer catheter with respect to the shaft 112. The handle assembly 114 includes a body 116 having a distal and proximal end 118, 120. The body 116 defines an interior lumen 122 extending through the proximal end 120 and through the distal end 118. The delivery device 110 further includes a guide wire 124 that is selectively directed through the lumen 122 of the handle assembly 114 and through the shaft 112. It is envisioned that the guide wire 124 can be provided separate from the delivery device 110. The guide wire 124 is threaded through the hollow shaft 112 to direct the prosthesis 111 to a target site at which the prosthesis 111 is to be deployed. In practice, an operator managing the shaft 112 controls the prosthesis 111 positioning. The delivery devices disclosed herein are configured to ergonomically also allow the operator to control the position of the guide wire as the position of the guide wire influences the deployment position of the prosthesis. In this way, a second operator for positioning the guide wire can be omitted. Embodiments of the disclosure are believed to improve positioning predictability and ease of use.

The delivery device 1110 includes a guide wire control 130 including an actuator 132 at the distal end 118 of the body 116 of the handle assembly 114. In some embodiments, the actuator 132 is positioned on the shaft 112. The actuator 132 is configured to control advancement of the guide wire 124. In one example, the actuator 132 has thumbwheel 134 secured to a slider 138 (schematically shown) that engages and advances the guide wire 124 routed through an opening or lumen 139 in the slider 138. One embodiment of this would be utilization of a rack and pinion mechanism where the thumbwheel 134 is the diving pinion and the rack is attached to the guide wire 124. Any other actuator capable of advancing the guide wire 124 and connection to the connector 140 is suitable.

The guide wire control 130 further includes a connector 140 extending through the lumen 122 of the body 116 and interconnecting the actuator 132 to a lock 142 that is positioned at a proximal end 120 of the body 116. The connector 140 can be welded or otherwise secured to both the actuator 132 and the lock 142. In one embodiment, the lock 142 is mounted to one or more support rods 143 extending from the proximal end 120. In various embodiments, the connector 140 includes a lumen 144 through which the guide wire 124 is routed. In such embodiments, the lumen 144 of the connector 140 is coaxial with the lumen 139 of the actuator/slider 138. In one embodiment, the connector 140 is not hollow but is a rod (i.e. stiff wire or rigid shaft) and the guide wire 124 is routed parallel to and spaced from the connector 140. Movement of the actuator 132 back and forth, via the thumbwheel 134 or the like correspondingly pulls and pushes the lock 142 and connector 140 with respect to the body 116 of the handle assembly 114 when the lock 142 is in the unlocked state.

The lock 142 includes a lumen or opening 146 through which the guide wire 124 is routed and is configured to have an unlocked state in which the guide wire 124 can move longitudinally through both the lumens 146, 122, 139 of the lock 142, the body 116 and slider 138. The lock 142 is further configured to have a locked state in which the guide wire 124 is locked and maintained in longitudinal position with respect to both the handle assembly 114 and the shaft 112. In one example of use, the lock 142 is left in its unlocked state until the shaft 112 is tracked and in its initial position, proximate a target site. The guide wire 124 is then locked with the lock 142 allowing an operator to take over from the patient side (i.e. distal end 118 of the handle assembly 114) allowing for single operator positioning control during prosthesis deployment. In one example, the lock 142 can be a Tuohy Borst type connector.

The devices (e.g., delivery device 110) of the disclosure can be used in methods of controlling a guide wire 124. The method can include providing the delivery device 110. The prosthesis 111, such as a stent or prosthetic heart valve, for example, can be provided on or collapsed onto the shaft 112. In this example, the guide wire control 130 is provided in the unlocked state. The method further includes positioning the guide wire 124 through the lumens 146, 122, 139 of the lock 142, handle assembly 114 and actuator 132 and directing the guide wire 124 into a vasculature of a patient proximate a target site by movement or other actuation of the actuator 132. In one example where the connector 140 includes a lumen 146, the guide wire 124 can also be routed through the connector 140. The shaft 112 is advanced along the guide wire 124 until the prosthesis 111 is guided to the target site for deployment. The method also includes transitioning the lock 142 to the locked state so that the longitudinal position of the guide wire 124 is maintained with respect to the handle assembly 114 and the shaft 112 during shaft/prosthesis 112/111 positioning and prosthesis 111 deployment.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A delivery device comprising:
   a handle assembly comprising a distal end and a proximal end, the handle assembly further including a body defining a lumen that extends from the distal end to the proximal end;
   a hollow shaft extending from the distal end of the handle assembly;
   a guide wire extending through the lumen; and
   a guide wire control, the guide wire control including an actuator positioned at the distal end of the handle assembly and a lock positioned at the proximal end of the handle assembly, the actuator interconnected to the lock with a connector positioned within the lumen, and the body of the handle assembly is positioned between the actuator and the lock with the actuator configured to be distally spaced from a distal end of the body, wherein the guide wire control comprises a locked state wherein a longitudinal movement of the actuator is configured to result in a corresponding longitudinal movement of the guide wire, the actuator, and the lock together as a unit relative to the body of the handle assembly, and the guide wire control further comprises an unlocked state in which the guide wire is configured to longitudinally move with respect to the actuator and the lock.

2. The delivery device of claim 1, wherein the actuator includes a slider mounted over the shaft.

3. The delivery device of claim 1, wherein the connector is a rigid shaft.

4. The delivery device of claim 1, wherein the connector is a tube.

5. The delivery device of claim 4, wherein the tube is a hypotube.

6. The delivery device of claim 4, wherein the guide wire is routed through the tube.

7. The delivery device of claim 4, wherein the tube extends from the distal end to the proximal end of the body of the handle assembly.

8. The delivery device of claim 1, wherein, in the locked state, a longitudinal movement of the actuator is configured to result in a corresponding longitudinal movement of the connector, the guide wire, the actuator, and the lock together as a unit.

9. The delivery device of claim 1, wherein the lock includes a Tuohy Borst connector.

10. The delivery device of claim 1, wherein the actuator is positioned on the shaft.

11. The delivery device of claim 1, wherein the actuator includes a thumbwheel.

12. A method of controlling a guide wire, the method comprising:
    providing a delivery device including:
        a handle assembly comprising a distal end and a proximal end, the handle assembly further including a body defining a lumen that extends from the distal end to the proximal end,
        a hollow shaft extending from the distal end of the handle assembly, and
        a guide wire control, the guide wire control including an actuator positioned at the distal end of the handle assembly and a lock positioned at the proximal end of the handle assembly, the actuator interconnected to the lock with a connector positioned within the lumen, and the body of the handle assembly is positioned between the actuator and the lock with the actuator configured to be distally spaced from a distal end of the body; wherein the guide wire control is provided in an unlocked state;
    positioning a guide wire through the lumen;
    directing the guide wire through the lumen and into a vasculature of a patient to a position proximate a target site by movement of the guide wire with respect to the actuator and the lock while the guide wire control is in the unlocked state;
    transitioning the guide wire control from the unlocked state to a locked state; and then
    longitudinally moving the actuator while the guide wire control is in the locked state, wherein the longitudinal movement of the actuator while the guide wire control is in the locked state results in a corresponding longitudinal movement of the guide wire, the actuator, and the lock together as a unit relative to the body of the handle assembly.

13. The method of claim 12, wherein the shaft is supporting a prosthesis, and the method comprises positioning the prosthesis at the target site.

14. The method of claim 13, further comprising directing the shaft to position the prosthesis.

15. The method of claim 12, wherein the connector comprises a rigid shaft.

16. The method of claim 12, wherein the connector comprises a tube.

17. The method of claim 12, wherein the actuator is positioned on the shaft.

18. The method of claim 12, wherein the actuator includes a slider mounted over the shaft.

19. The method of claim 12, wherein the actuator includes a thumbwheel.

20. The method of claim 12, wherein longitudinally moving the actuator while the guide wire control is in the locked state, further results in a corresponding longitudinal movement of the connector, guide wire, actuator, and the lock together as a unit.

* * * * *